United States Patent [19]

Masiz

[11] Patent Number: 5,645,854
[45] Date of Patent: *Jul. 8, 1997

[54] MOLECULAR TRANSDERMAL TRANSPORT SYSTEM

[76] Inventor: John J. Masiz, 26 High St., Topsfield, Mass. 01983

[*] Notice: The term of this patent shall not extend beyond the expiration date of Pat. No. 5,460,821.

[21] Appl. No.: 542,068

[22] Filed: Oct. 12, 1995

Related U.S. Application Data

[63] Continuation-in-part of Ser. No. 227,365, Apr. 13, 1994, Pat. No. 5,460,821, which is a continuation-in-part of Ser. No. 81,567, Jun. 23, 1993, abandoned.

[51] Int. Cl.$^6$ .................................................. A61F 13/00
[52] U.S. Cl. ........................ 424/449; 424/447; 514/946; 514/947
[58] Field of Search ................................ 424/499, 447; 514/946, 947

[56] References Cited

U.S. PATENT DOCUMENTS

| | | | |
|---|---|---|---|
| 4,788,061 | 11/1988 | Shore | 424/448 |
| 4,910,020 | 3/1990 | Samour | 424/448 |
| 4,933,184 | 6/1990 | Tsuk | 424/449 |
| 5,229,130 | 7/1993 | Sharma et al. | 424/449 |

OTHER PUBLICATIONS

The Merck Index, Tenth Edition. 1983 pp. 260, 660 & 14444.

*Primary Examiner*—Gabrielle Phelan
*Attorney, Agent, or Firm*—Nields & Lemack

[57] ABSTRACT

An efficient transdermal delivery system for delivering an active ingredient to the blood supply of a living body, comprising a vasodilator and/or topical counter irritant, an active ingredient, a permeation enhancer for the active ingredient, and a water soluble gum for binding the foregoing. A non-breathable layer also can be used for controlling the microenvironment at the transport site. Compression can be used to further enhance the blood supply at the transport site.

17 Claims, No Drawings

MOLECULAR TRANSDERMAL TRANSPORT SYSTEM

This application is a continuation-in-part of U.S. Ser. No. 227,365 filed Apr. 13, 1994, now U.S. Pat. No. 5,460,821, which is a continuation-in-part of U.S. Ser. No. 081,567 filed Jun. 23, 1993 (abandoned).

BACKGROUND OF THE INVENTION

Transdermal drug delivery offers many advantages over other types of drug delivery. With transdermal delivery, a localized delivery of drug molecules can be achieved, which makes transdermal drug delivery target specific. Further, transdermal drug delivery avoids the gastro intestinal complications caused by oral delivery. While transdermal drug delivery offers these and other advantages, a system than can quickly and reliably deliver predictable quantities of drug molecules through the skin has heretofore not been developed.

The evolution of transdermal drug delivery has centered around patch technology. Patch technology is based on the ability to hold an active ingredient in constant contact with the epidermis. Over substantial periods of time, drug molecules, held in such a state, will eventually find their way into the bloodstream. Thus, patch technology relies on the ability of the human body to pick up drug molecules through the skin. Transdermal drug delivery using patch technology has recently been applied for delivery of nicotine, in an effort to assist smokers in quitting, the delivery of nitroglycerine to angina sufferers, the delivery of replacement hormones in post menopausal women, etc. These conventional drug delivery systems comprise a patch with an active ingredient such as a drug incorporated therein, the patch also including an adhesive for attachment to the skin so as to place the active ingredient in close proximity to the skin.

Problems with patch technology abound. First, active drug molecules have a difficult time passing through the skin, as the skin poses a significant barrier. In fact, in order for a drug molecule to reach the bloodstream, it must pass through the epidermis, stratum corneum (an especially dense layer of cells), dermis and capillary cell structure. Second, real world conditions such as the patient's obesity, metabolism and circulatory efficiency can effectively prevent transdermal drug delivery from occurring. Third, patch technology can be used only for treatments involving extensively long treatment periods, since the flow rate of drug molecules is so small. Finally, patch adhesion to the skin causes extensive skin trauma as well as cosmetic problems. Specifically, most adhesives currently used tend to aggressively adhere to the skin so that their removal may cause irritation and trauma. Indeed, subsequent patches used by a given individual are often applied to a different area of the skin in order to minimize such irritation and trauma.

In an effort to enhance the efficiency of transdermal drug delivery, the prior art teaches that by mixing certain individual ingredients (penetration enhancers) with a drug molecule, the ability of the drug molecule to pass through the skin is increased somewhat. For example, U.S. Pat. No. 4,933,184 discloses the use of menthol as a penetration enhancer; U.S. Pat. No. 5,229,130 discloses the use of vegetable oil (soybean and/or coconut oil) as a penetration enhancer; and U.S. Pat. No. 4,440,777 discloses the use of eucalyptol as a penetration enhancer.

Although mixing a penetration enhancer with a drug molecule helped to somewhat increase the speed of drug delivery, problems were still present. First, the aforementioned penetration enhancers constitute a passive, not an active, system. Thus, since they were not linked to the drug active molecule, the penetration of the enhancer does not necessarily mean that the drug molecule has penetrated. In fact, the prior art drug molecule penetration is only a by-product of the enhancer penetration. Second, even when drug molecule penetration has occurred, the prior art does not establish a condition whereby the blood supply to the transport area is enhanced so as to maximize absorption speed. Third, prior art does not create a molecular structure that releases the drug molecule readily upon contact of acidic or alkaline bodily fluids so as to maximize bioavailability of the drug. Finally, although the prior art has increased the speed of transport of the drug molecule transdermally, it is still not sufficiently fast so as to eliminate (if desired) the need for a patch.

It is therefore an object of the present invention to provide a transdermal transport system that efficiently and easily allows for effective delivery of an active ingredient through the skin and into the blood supply of an animal or human.

SUMMARY OF THE INVENTION

The problems of the prior art have been overcome by the present invention, which provides an efficient, predictable and reliable active ingredient transdermal delivery system that is sufficiently fast so as to eliminate (if desired) the need for a patch. More specifically, the present invention creates a molecular transdermal delivery vehicle that contains, as an integral part of the transdermal delivery molecule, the active drug molecule. This molecularly uninhibited lacteal ensemble (or "MULE") is constructed of four elements, namely, a vasodilator, a penetration enhancer, the active ingredient, and a water soluble gum for linking the vasodilator, penetration enhancer and active ingredient.

The advantages of the present invention over the prior art are many. First, the creation of a singular molecular unit that contains the drug molecule and transdermally transports it constitutes the first active system. Unlike the prior art, any degree of molecular penetration directly correlates to drug molecule penetration, hence it is also predictable. Second, the MULE enhances blood flow to the transport/application site. Regardless of metabolism, obesity or circulatory efficiency, the vasodilatory aspect of the MULE maximizes blood flow to the transport site so as to reliably maximize absorption of the drug molecule. Third, the MULE is constructed in a manner that when exposed to bodily fluids that are non-neutral mn pH (i.e., have pH's that are less than or greater than 7.0), it breaks apart, thereby releasing the drug molecule. This event insures bioavailability so that drug molecules are exposed to the blood supply and are capable of being picked up. Finally, the present invention operates on transport speed that eliminates (if desired) the need for a patch.

DETAILED DESCRIPTION OF THE INVENTION

The invention comprises the creation of a molecular transdermal transport vehicle for mammals that has at least four components, including the active ingredient.

The first element of the MULE is one that enhances blood flow, through vasodilatory action, and/or through counter irritational action at the transport site. For example, topical counter irritants can be used, which are substances that provide a mild dermal irritation, generally creating a hot or cold sensation in the area of application. This sensation results from the fact that the mild skin irritation brings blood closer to the surface of the skin, and can be utilized to enhance blood supply and effective transport of the active ingredient/carrier. Suitable ratios of vasodilators/counter irritants in the MULE range from about 1% to about 80% by weight, with ratios of from about 1% to about 33% being preferred. The amount of vasodilator/counter irritant will vary due to a number of factors, including the drug molecule size, drug concentration, the desired delivery speed, the size of the surface area of an application, and the application site. Excess amounts of vasodilators/counter irritants can be used without impacting the performace of the MULE. In one embodiment, the nature and concentration of the counter irritant in the MULE are those established by the Food and Drug Administration in the topical analgesic/topical counter irritant monographs for over-the-counter drugs, which monographs are herein incorporated by reference. For example, the counter irritants can be used in an amount effective for causing an irritation, such as about 1% in the case where natural menthol is used as an external analgesic, and about 1–10% where natural menthol is used as a topical counter irritant. In another embodiment, the concentration of the counter irritant can be considerably higher. For example, 11–80% by weight may be suitable, more preferably 11–33% by weight. Suitable applications utilizing the higher amounts of counter irritant include applications in which non-steroidal anti-inflammatories such as aspirin, ibuprofen, FELDENE®, VOLTAREN®,etc. are the active ingredient. Suitable vasodilators or counter irritants include menthol, methyl salicylate, oil of wintergreen, peppermint oil, and capsisium, with menthol being preferred.

The second element of the MULE is an ingredient that functions as a permeation or penetration enhancer. Suitable enhancers include vegetable oil or a vegetable oil/alcohol mix. Suitable vegetable oils include peanut oil, olive oil, sunflower oil, soybean oil, monoi oil and macadamia oil, with olive oil being preferred. Suitable alcohols for the vegetable oil/alcohol mix include ethyl alcohol, isopropyl alcohol, methanol and witch hazel. Olive oil mixed with isopropyl alcohol is a preferred vegetable oil/alcohol mix. Eucalyptol is a further suitable example of a vegetable oil/alcohol mix. Suitable ratios of vegetable oil:alcohol range from about 5:1 to about 1:10, preferably 1:2. Suitable amounts of vegetable oil or vegetable oil/alcohol mix in the MULE range from about 1% to about 66% by weight, more preferably from about 10% to about 33.3% by weight. The third element of the MULE is the active ingredient. The term "active ingredient" is used herein to indicate any material or composition desired to be delivered transdermally, especially drugs. Examples of active ingredients that can be used in accordance with the present invention include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, °6X chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofuwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyldopa, methylergonovine, methylphenidate, methylprednisolone, methysergide, metoclopramide, metolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystatin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, psyllium, pyridostigmine, pyrodoxine, pyrilamine, pyrvinium, quinestrol, quinethazone, quinidine, quinine, ranitidine, rauwolfia alkaloids, riboflavin, rifampin, ritodrine, salicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B-12, vitamin C, vitamin D, vitamin E, vitamin K and xanthine.

The final element that is essential to the creation of the MULE is the addition of a water soluble gum. The water soluble gum binds the first three elements of the MULE together into the singular transport vehicle, and releases the active ingredient upon exposure to a fluid with a non-neutral pH. Suitable bodily fluids with a non-neutral pH include blood, interstitial fluid, sweat, saliva, mucoid secretions, lymphatic fluid, oil, gastric juices, pericandial fluid, sinovial fluid (inter-joint), intercranial fluid, endolymph, perilymph, synpatic fluid, intersynaptic fluid, and cerebrospinal fluid. Suitable water-soluble gums include agar, arabic, carob, CMC, carrageenans, ghatti, guar, karaya, kadaya, locust bean, tragacanth and xanthan gums. The water soluble gum should be used in an amount ranging from about 1% to about 33.3% by weight, most preferably an amount equal to the amount of active ingredient used.

The MULE is created by placing the penetration enhancer, the vasodilatory and/or counter irritant, and the active ingredient in a mixing vessel, and agitating the combination over a sufficient period to achieve a uniform mix. The water soluble gum is then slowly added while continuing the agitation. After completion of the gum addition, agitation continues until mix uniformity is achieved. Other inactive ingredients may be added if desired.

Although the MULE transports drug molecules so efficiently that the need for a patch is obviated, a patch can still be used where desired. Pre-packaged patches, pre-impregnated with the MULE can make prescribed doses controllable. However, if a patch is used in conjunction with the MULE of the present invention, preferably the patch is a non-breathable layer on which the active ingredient is placed. Suitable non-breathable layers include sheets of plastic, polyethylene, polyvinyl chloride, wax paper, foil, latex, etc., and combinations thereof. Those skilled in the art will recognize that any non-breathable substance (defined as a substance that does not allow the exchange of gases through its membrane) that is not deleterious to the particular active ingredient being used and that does not cause any irritation upon contact with skin can be used.

The non-breathable layer functions to create and control a suitable microenvironment at the transport site. Too cold an environment can result in little blood supply to the dermal barrier; pores and other natural openings in the dermal barrier constrict, thereby preventing efficient transport. Too hot an environment can enhance secretion and perspiration and vapor flow through the dermal barrier, creating negative transport activity. Too dry an environment can cause an element or elements of the MULE to evaporate quickly, losing its ability to transport. The enhanced evaporation also creates negative transport pressure. Too humid an environment can cause dilution of the active ingredient, diminishing the capacity of the active ingredient and also creating negative transport activity.

The non-breathable layer captures the body temperature and humidity, thereby maintaining temperature at the most efficient for transport, the pore size at or close to a maximum, and normal blood flow to the site. In addition, since body vapor is captured, a proper moisture level is maintained. Preferably the temperature and humidity at the transport site is about 85°–100° F. and 50–99%, respectively. The non-breathable layer also creates a positive osmotic pressure back through the dermal layer, acting in a manner analogous to the so-called "greenhouse effect". Vapor admitted through the skin passes through the MULE, collects along the non-breathable barrier and then passes back through the MULE and through the skin. Since the temperature is at about the body temperature, the pore size is maximized and blood flow is sufficient so that the active ingredient can be easily picked up by the blood through the dermal layer. If desired, the non-breathable layer can be secured to the skin by any suitable means, such as with a bandage having adhesive or fasteners. In the preferred embodiment, no adhesive is used, instead compression is used as discussed in detail below.

In order to further enhance blood supply to the transport site, compression can be utilized. Specifically, the non-breathable layer can be applied to the skin tightly, such as with a tightly wrapped bandage. Preferably the compression at the transport site is greater than zero pounds per square inch but less than about 10 pounds per square inch. Too much compression can result in restricted blood supply. The positive pressure applied also aids in forcing the MULE through the dermal layer and into contact with the blood supply.

The non-breathable layer and wrapping material can be conveniently designed to accommodate specific transport sites. For example, the non-breathable layer and wrap can be shaped in the form of a glove to be worn on one hand of the individual, or can be shaped in the form of a band to be worn on the arm or leg of the individual.

EXAMPLE 1

Vegetable oil, natural menthol and the active ingredient are placed in a mixing vessel. The contents are then agitated therein to achieve a uniform blend. Xanthan gum is then added slowly with the mixing vessel contents being continually agitated. The agitation continues until a uniform blend is achieved. Other inactive ingredients may be added, and again the contents mixed until uniformity is achieved.

The contents are removed from the mixing vessel and are applied directly to the skin at the desired transport site by gentle massaging for approximately 60 seconds or until the mixture disappears.

What is claimed is:

1. A transdermal delivery system for delivering an active ingredient through the skin of a living body, comprising:

a. an active ingredient;

b. first means for enhancing the blood supply to the site of transport of said active ingredient through said skin, said first means comprising a topical counter irritant;

c. second means for enhancing the permeation of said active ingredient through said skin; and d. third means for binding said active ingredient and said first and second means into a singular transport vehicle, said third means releasing said active ingredient upon contact with a bodily fluid that has a non-neutral pH.

2. The transdermal delivery system of claim 1, wherein said topical counter irritant is selected from the group consisting of menthol, methyl salicylate, oil of wintergreen, peppermint oil and capsisium.

3. The transdermal delivery system of claim 1, wherein said second means for enhancing the permeation comprises a vegetable oil.

4. The transdermal delivery system of claim 2, wherein said second means for enhancing the permeation comprises a vegetable oil.

5. The transdermal delivery system of claim 3, wherein said second means is selected from the group consisting of peanut oil, olive oil, sunflower oil, soybean oil, monoi oil, macadamia oil and a vegetable oil/alcohol mix.

6. The transdermal delivery system of claim 4, wherein said second means is selected from the group consisting of peanut oil, olive oil, sunflower oil, soybean oil, monoi oil, macadamia oil and a vegetable oil/alcohol mix.

7. The transdermal delivery system of claim 1, wherein said third means comprises a water-soluble gum.

8. The transdermal delivery system of claim 2, wherein said third means comprises a water-soluble gum.

9. The transdermal delivery system of claim 4, wherein said third means comprises a water-soluble gum.

10. The transdermal delivery system of claim 7, wherein said water-soluble gum is selected from the group consisting of agar, arabic, carob, CMC, carrageenans, ghatti, guar, karaya, kadaya, locust bean, tragacanth and xanthan gum.

11. The transdermal delivery system of claim 8, wherein said water-soluble gum is selected from the group consisting of agar, arabic, carob, CMC, carrageenans, ghatti, guar, karaya, kadaya, locust bean, tragacanth and xanthan gum.

12. The transdermal delivery system of claim 9, wherein said water-soluble gum is selected from the group consisting of agar, arabic, carob, CMC, carrageenans, ghatti, guar, karaya, kadaya, locust bean, tragacanth and xanthan gum.

13. The transdermal delivery system of claim 1, further comprising means for controlling the temperature and humidity at the site of transport of said active ingredient through said skin, said means comprising a non-breathable layer.

14. The transdermal delivery system of claim 1, wherein said non-neutral medium is selected from the group consisting of blood, interstitial fluid, sweat, saliva, mucoid secretions, lymphatic fluid, sinovial fluid, endolymph, perilymph, synaptic fluid, intersynaptic fluid, and spinal fluid.

15. A method of delivering an active ingredient through the skin of a living body, comprising:

a. placing the active ingredient on the skin at a transport site;

b. enhancing the blood supply to the site of transport of said active ingredient through said skin by causing a skin irritation at said site by applying a topical counter irritant to said site;

c. enhancing the permeation of said active ingredient through said skin by binding said active ingredient to a carrier with a water-soluble gum; and d. allowing said active ingredient to be released from said carrier upon contact with a bodily fluid having a non-neutral pH.

16. The method of claim 15, wherein said non-neutral medium is selected from the group consisting of blood, interstitial fluid, sweat, saliva, mucoid secretions, lymphatic fluid, sinovial fluid, endolymph, perilymph, synaptic fluid, intersynaptic fluid, and spinal fluid.

17. The method of claim 15, further comprising controlling the temperature and humidity at said transport site by covering said transport cite with a non-breathable layer.

\* \* \* \* \*